United States Patent [19]
Silvis

[11] Patent Number: 5,968,452
[45] Date of Patent: *Oct. 19, 1999

[54] SYSTEM FOR CONTROLLING FLOW OF A DILUTED SAMPLE AND DETERMINING POLLUTANTS BASED ON WATER CONTENT IN ENGINE EXHAUST EMISSIONS

[76] Inventor: William M. Silvis, 840 Watershed, Ann Arbor, Mich. 48105

[*] Notice: This patent is subject to a terminal disclaimer.

[21] Appl. No.: 09/121,427

[22] Filed: Jul. 23, 1998

Related U.S. Application Data

[62] Division of application No. 08/831,320, Apr. 1, 1997, Pat. No. 5,846,831.

[51] Int. Cl.$^6$ ..................................................... G01N 31/12
[52] U.S. Cl. ................................ 422/62; 422/83; 422/94; 436/55; 436/155; 436/158; 436/160; 73/23.21; 73/23.31; 73/863.03
[58] Field of Search ................................... 436/55, 39, 52, 436/116, 122, 134, 155, 158, 160; 422/62, 83, 94; 73/23.21, 23.31, 29.01, 31.03, 863.03

[56] References Cited

U.S. PATENT DOCUMENTS

| | | |
|---|---|---|
| 3,144,769 | 8/1964 | Francisco, Jr. . |
| 3,407,646 | 10/1968 | Traver . |
| 3,593,023 | 7/1971 | Dodson . |
| 3,603,315 | 9/1971 | Morris . |
| 3,699,814 | 10/1972 | Kaufman . |
| 3,784,902 | 1/1974 | Huber . |
| 3,817,100 | 6/1974 | Anderson et al. . |
| 3,895,915 | 7/1975 | Haldeman . |
| 3,965,749 | 6/1976 | Hadden et al. . |
| 3,986,386 | 10/1976 | Beltzer et al. . |
| 4,222,667 | 9/1980 | Lewis et al. . |
| 4,254,797 | 3/1981 | Mayeaux . |
| 4,351,181 | 9/1982 | Currans . |
| 4,379,402 | 4/1983 | Harman, III . |
| 4,498,496 | 2/1985 | Barcellona et al. . |
| 4,555,930 | 12/1985 | Leach et al. . |
| 4,555,931 | 12/1985 | Amimoto et al. . |
| 4,586,367 | 5/1986 | Lewis . |
| 4,660,408 | 4/1987 | Lewis . |

(List continued on next page.)

OTHER PUBLICATIONS

Database CAS on STN (Columbus, Ohio), CA 103:26418, Summers et al. Integrated exhaust gas analysis system for aircraft turbine engine component testing,' abstract, Report (1985), NASA–TP–2424, E–2302, NAS1.60:2424, 28 pp. (Avail: NTIS).

*Primary Examiner*—Jan Ludlow

[57] ABSTRACT

A system is provided in an exhaust emission sampling system for controlling a flow controller in order to compensate for the effects of changing water vapor content in a diluted sample having a predetermined dilution ratio. A water measuring device such as a relative humidity sensor generates a water vapor signal based on the amount of water vapor in the diluted sample. The water vapor signal is then processed within a control unit to obtain a value for the amount of water in the diluted sample. A control signal is generated by the control unit based on the amount of water vapor, flow rate of the exhaust emissions, and also, on the type of fuel used in the combustion process to control the flow controller which is, preferably, a mass flow controller. A second system is provided in an exhaust emission analyzing system for determining a final amount of pollutants also compensated for the effects of changing water vapor content in the exhaust emissions. The control unit not only processes the water vapor signal from the sensor to obtain a value for the amount of water vapor in the diluted sample as in the first embodiment, but also generates a correction factor based on the value. The correction factor is then utilized by a computer to calculate a final amount of the pollutants based on the correction factor and a preliminary amount of pollutants determined by analyzers of the exhaust emission analyzing system.

3 Claims, 2 Drawing Sheets

U.S. PATENT DOCUMENTS

| | | |
|---|---|---|
| 4,823,591 | 4/1989 | Lewis . |
| 4,852,384 | 8/1989 | Woolbert et al. . |
| 4,977,776 | 12/1990 | Shindo et al. . |
| 5,129,257 | 7/1992 | Varduner et al. . |
| 5,157,957 | 10/1992 | Mettes et al. . |
| 5,184,501 | 2/1993 | Lewis et al. . |
| 5,217,692 | 6/1993 | Rump et al. . |
| 5,267,467 | 12/1993 | Caron . |
| 5,279,146 | 1/1994 | Asano et al. . |
| 5,337,595 | 8/1994 | Lewis . |
| 5,410,907 | 5/1995 | Strom et al. . |
| 5,469,731 | 11/1995 | Decker et al. . |
| 5,485,754 | 1/1996 | Harpster . |

SYSTEM FOR CONTROLLING FLOW OF A DILUTED SAMPLE AND DETERMINING POLLUTANTS BASED ON WATER CONTENT IN ENGINE EXHAUST EMISSIONS

CROSS-REFERENCE TO RELATED APPLICATION

This is a divisional of application Ser. No. 08/831,320 filed on Apr. 1, 1997 now U.S. Pat. No. 5,846,831.

This application is related to application entitled "Method and Apparatus for Providing Diluent Gas to Exhaust Emission Analyzer" filed on Sep. 29, 1995 in the name of R. Neal Harvey et al., and having U.S. Ser. No. 08/536,401 now U.S. Pat. No. 5,756,360.

TECHNICAL FIELD

This invention relates to methods and systems for controlling flow of a diluted sample and determining pollutants based on water content in engine exhaust emissions and, in particular, to a method and system for controlling a flow controller and for determining final amount of pollutants by compensating for the effects of changing water vapor content in engine exhaust emissions.

BACKGROUND ART

The constant volume sampler (i.e. CVS) was first applied in the late 1950's to make possible the measurement of the mass of exhaust emissions. Before that time, emissions tests had been based on concentration limits. Since the effect on the environment is assessed by the grams of pollutants emitted by vehicles per mile driven, a sampling system was needed that could measure the mass of these emissions while the vehicle was operated through a sequence of accelerations and decelerations that approximated normal driving.

Figure 1:
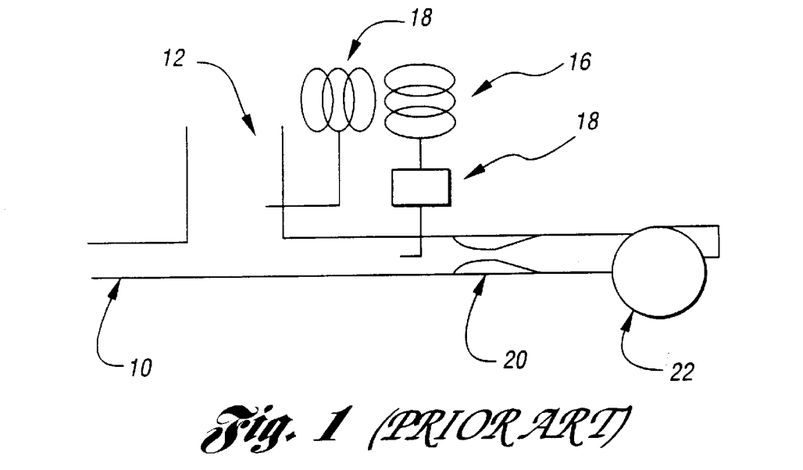
FIG. 1 is a schematic block diagram of a prior art CVS.

The CVS and its operation are illustrated in FIG. 1 wherein vehicle exhaust enters the CVS at inlet 10, ambient air for dilution enters at 12, and ambient bags and sample bags are indicated at 14 and 16, respectively. The CVS also includes a sample flow pump and a controller 18, a measuring device 20 such as a CFV or SAO to measure CVS flow to calculate volume, and a blower or pump 22 to set CVS flow rate.

All of the vehicle's exhaust is diluted with ambient air in the relatively large mixing "T" of FIG. 1. The combined gases are drawn through the system by the blower or pump 22 at a relatively constant combined flow rate. Thus, a CVS operates at a variable dilution ratio. As the vehicle produces more exhaust, less ambient air is mixed with it in order to keep the total flow constant.

The measuring or metering device 20 in the bulk stream determines the flow rate. In this manner, the total volume of the mixture is easy to determine from the time of the sampling multiplied by the constant flow rate. Today, CVS units actually do not quite operate at a constant rate of flow, but the name CVS is still used.

A small, proportional sample of the diluted gases is collected in the sample bags 16 during the sampling period. The sample bags 16 are analyzed later for the concentrations of the pollutants. A simultaneous sample of the dilution air is also collected in the bag 14 for subsequent analysis.

There are several types of CVS units available today, including fixed flow PDP and CFV types as well as variable flow SAO types.

The requirements of testing low emission vehicles make better sampling systems necessary. Vehicles today may use alternative fuels such as Methanol, CNG and LPG. Burning these fuels produces more water, requiring more dilution, which lowers sample concentrations.

However, the same vehicles are likely to be LEVs and ULEVs, low and ultra low emission vehicles. The emissions from these vehicles are very low, and the concentrations have become very difficult to measure accurately. It is clearly important not to over-dilute these samples, making them even more difficult to measure.

To meet these conflicting requirements, a CVS needs to operate at the correct flow rate for each vehicle, fuel and ambient condition. CVS units based on fixed flow metering orifices however, are only able to operate at a relatively small number of fixed flow rates.

At this point, the CVS method is very near its limit of capability for accurate measurement of low amounts of pollution. The basic limitation arises from the method for diluting the exhaust gases. The only diluent available in sufficient quantity to be practical in a CVS is the ambient air in the test cell. However, this gas already contains considerable water and has background concentrations of the pollutants that can be as large as the concentrations coming from the vehicle. So the CVS must dilute the exhaust gases more than necessary with contaminated diluent. The sample concentrations that result are too low to be conveniently analyzed with conventional gas analyzers and the need to compensate for an almost equal amount of pollutant contributed by the background doubles the uncertainty of the measurement.

Figure 2:
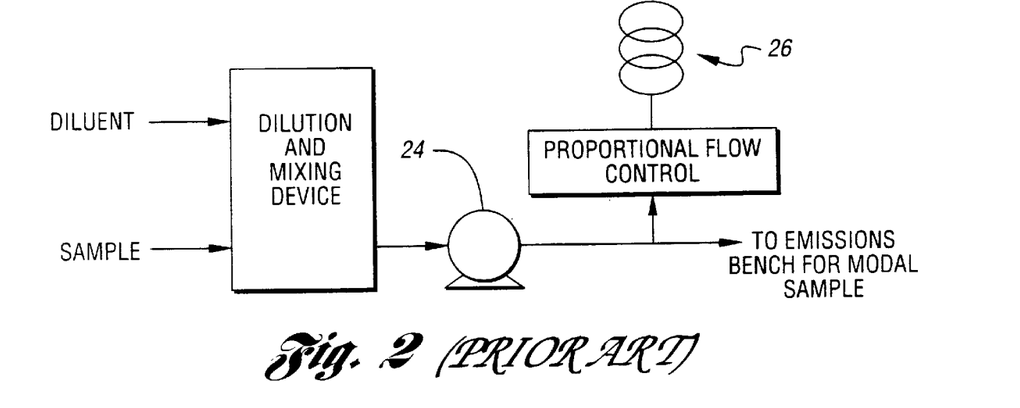
FIG. 2 is a schematic block diagram of a prior art mini-diluter.

Mini-diluters are a new class of devices that avoid these limitations by reversing the order of the diluting and sampling of the exhaust gases, as shown in FIG. 2. The mini-diluter of FIG. 2 includes a pump 24 and sample bags 26.

As previously mentioned, while a CVS system must dilute all of the vehicle's exhaust at a variable dilution ratio, and then take a proportional sample, a mini-diluter reverses this process by first taking a small sample of the exhaust gas and then accurately diluting it at a relatively constant dilution ratio. Since only a small volume of diluent is needed, a dry, contaminant free gas, dry air or nitrogen, can be used. Two advantages are the higher, more easily measured concentrations resulting from less dilution and the absence of background contaminants, eliminating a need for a separate, error prone analysis of the background pollution. The collection and analysis of samples of the diluent air is eliminated, doubling the accuracy of the mass calculation.

A challenge for the mini-diluter is that the rate of collected sample over a test period must be kept proportional to the raw exhaust flow from the vehicle, which is strongly varying, instead of the bulk stream flow through the CVS, which is relatively constant.

The following table illustrates the improvement in accuracy that can be expected with a mini-diluter. It shows the expected sample bag concentrations for a vehicle getting 25 mpg tested at 50% relative humidity at 74° F. that meets the required ULEV emissions levels. The table compares the resulting bag concentrations for a standard CVS with fixed flow at 320 cfm, as referenced in the Code of Federal Regulations, a variable flow CVS, optimized for these conditions, and for a mini-diluter.

| Expected Bag Concentrations | | | | |
|---|---|---|---|---|
| | ULEV Limit | CVS | VFCVS | Mini-Diluter |
| HC | 0.040 g/mi | 1.1 ppm | 1.9 ppm | 3.3 ppm |
| CO | 1.70 g/mi | 22.7 ppm | 39.1 ppm | 70.1 ppm |
| $NO_x$ | 0.20 g/mi | 1.6 ppm | 2.8 ppm | 5.0 ppm |

It can be observed that the mini-diluter technique raises the bag concentrations enough that it is feasible to measure these levels with the same analyzer technology that is in use today.

All these sampling systems, fixed and variable flow CVS's as well as mini-diluter, must perform the following three functions:

Prevent condensation of water in the sample before it can be measured. The water content creates two problems. First, water condensing during the analysis process changes the concentration or the volume of the sampled gases, affecting the accuracy of the result. Second, some contaminants, such as formaldehyde and $NO_x$, are affected by the removal of water.

Measure the total gas volume over a sampling interval, so the mass of emissions can be calculated.

Collect a proportional sample of diluted exhaust in a sample bag for analysis. At any time, the rate of flow of sampled gases and the total rate of flow of diluted exhaust through the CVS must be in the same proportion.

Figure 3:
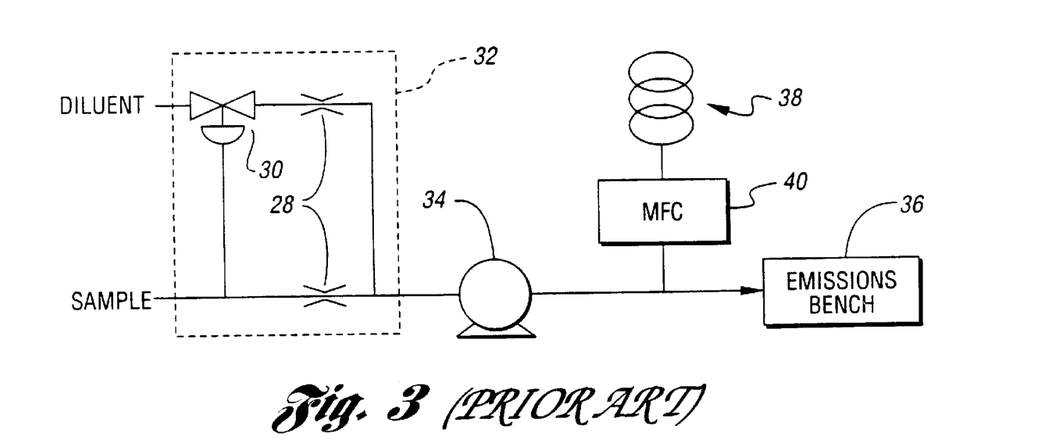
FIG. 3 is a schematic block diagram of another mini-diluter having a mass flow controller.

An improved mini-diluter of the above-noted patent application is illustrated in FIG. 3. The mini-diluter of FIG. 3 includes critical flow orifices (CFO's) 28 to establish a stable dilution ratio. One of the orifices 28 is for the diluent, either nitrogen or dry air, and the other of the orifices 28 is smaller and is for the sample gas. The orifices 28 operate on the principle from fluid dynamics that the flow through an orifice reaches a known maximum flow when the pressure drop across it is large enough that the velocity in the orifice throat reaches the speed of sound. The two orifices 28 are appropriately sized to provide a fixed dilution ratio appropriate for the type of fuel being used.

A modified pressure regulator 30 of the mini-diluter maintains equal pressure at the inlets of the two orifices 28, even as the conditions at the sampling point may change. A reference port is connected to the sample inlet and the action of the regulator 30 keeps the pressure at the inlet of the diluent orifice equal to the pressure at the inlet to the sample orifice.

The wet raw gases are brought to the dilution component via heated lines, and the orifices 28 and pressure regulator 30 are kept in an oven 32 to prevent any condensation of the sample before it is diluted. The oven 32 also keeps the inlet temperatures of both orifices 28 at the same temperature. Together with the action of the pressure regulator 30, this keeps the dilution ratio relatively constant.

The diluted gases can then be pumped by a pump 34 and then routed to either a conventional analyzer bench 36 for a modal analysis or sent to sample bags 38. When used for modal sampling, the mini-diluter replaces the usual sample conditioning unit, providing the advantages of much less extracted sample and no modification of the sample by a cooler.

A mass flow controller 40 having a control valve (not shown) is used to proportion the flow to the bags 38. The absolute accuracy of the mass flow controller 40 is not critical, only that its flow be kept in proportion to the vehicle exhaust flow. It is also important to compensate for the gas transport delays from the sample point to the flow controller 40 so that the desired weighting of the collected gases is correct.

As noted above, one approach to implementing a mini-diluter has been to use mass flow controllers, such as commonly used in the semiconductor industry, to control the rates of flow of raw exhaust sample, diluent gas and proportional diluted sample. However, early attempts have not yet been entirely successfully demonstrated to be equivalent to the CVS method. The stability of the mass flow controllers and the sensitivity of their controlled flow rate to the composition of the flowing gases, as well as their slower response times to sudden changes in desired flow, have presented difficulties.

One of the difficulties of sampling exhaust, which others may not fully appreciate, is the changing water content of the sample. A key realization is that water is lost from the exhaust gas even inside the vehicle exhaust manifolds and piping, before it is even available to be sampled, even by a mini-diluter using heated sampling lines. An engine is initially cold when testing begins and it is during this relatively brief period that most of the pollutants are emitted. It is also during this period that the inaccuracies caused by lost water vapor from condensation in the exhaust manifolds and tailpipes have their greatest influence on the performance of the active elements of the mini-diluter.

The critical flow orifices 28 of FIG. 3 are affected by the changing water content of the exhaust gases, but to a much lesser extent than are the thermo-dynamic elements of a mass flow controller. The mass flow controller 40 of FIG. 3 is utilized only to proportion the sample to the exhaust flow. The absolute accuracy of the flow is not important, since this flow does not need to be measured.

SUMMARY OF THE INVENTION

An object of the present invention is to provide a method and system for controlling a flow controller such as a mass flow controller in an exhaust emission sampling system based on changing water content of a sample of the exhaust emissions.

Another object of the present invention is to provide a method and system for determining final amount of pollutants in an exhaust emission analyzing system based on changing water content of a sample of the exhaust emissions.

Still another object of the present invention is to provide a method and system for controlling flow of a diluted sample having a predetermined dilution rate in an exhaust emission sample system so that the predetermined dilution ratio is held relatively constant despite changing water content in the diluted sample.

In carrying out the above objects and other objects of the present invention in an exhaust emission sampling system including a flow controller for controlling the flow of a diluted sample of exhaust emissions from an engine's combustion process, the diluted sample having a predetermined dilution ratio, a method is provided for controlling the flow controller in order to compensate for the effects of changing water vapor content in the diluted sample. The method includes the steps of generating a water vapor signal based on the amount of water vapor in the diluted sample and processing the water vapor signal to obtain a value for the amount of water vapor in the diluted sample. The method also includes the step of generating a control signal based on the value to control the flow controller which, in turn, controls the flow of the diluted sample.

Preferably, the step of generating the control signal is also based on the flow rate of exhaust emissions and the type of fuel used in the combustion process.

Also, preferably, the step of generating the water vapor signal includes the step of sensing humidity in the flowing diluted sample.

Further in carrying out the above objects and other objects of the present invention in an exhaust emission sampling system including a flow controller for controlling the flow of a diluted sample of exhaust emissions from an engine's combustion process, the diluted sample having a predetermined dilution ratio, a control system is provided for controlling the flow controller in order to compensate for the effects of changing water vapor content in the exhaust emissions. The control system includes a measuring device for generating a water vapor signal based on the amount of water vapor in the diluted sample. The control system also includes a control unit for processing the water vapor signal to obtain a value for the amount of water vapor in the diluted sample and for generating a control signal based on the value to control the flow controller which, in turn, controls the flow of the diluted sample.

Preferably, the control unit generates the control signal also based on the flow rate of the exhaust emissions and the type of fuel used in the combustion process.

Still further in carrying out the above objects and other objects of the present invention in an exhaust emission analyzing system including an exhaust emission analyzer for analyzing a diluted sample of exhaust emissions from an engine's combustion process to obtain a preliminary amount of pollutants, a method is provided for determining a final amount of pollutants compensated for effects of changing water vapor content in the exhaust emissions. The method includes the steps of generating a water vapor signal based on the amount of water vapor in the diluted sample, processing the water vapor signal to obtain a value for the amount of water vapor in the diluted sample, and generating a correction factor based on the value. The method also includes the step of calculating the final amount of pollutants based on the correction factor and the preliminary amount of pollutants.

Preferably, the step of generating the water vapor signal includes the step of sensing humidity in the flowing diluted sample.

Yet still further in carrying out the above objects and other objects of the present invention in an exhaust emission analyzing system including an exhaust emission analyzer for analyzing a diluted sample to obtain a preliminary amount of pollutants, a determining system is provided for determining a final amount of pollutants compensated for the effects of changing water vapor content in the exhaust emissions. The determining system includes a measuring device for generating a water vapor signal based on the amount of water vapor in the diluted sample and a control unit for processing the water vapor signal to obtain a value for the amount of water vapor in the diluted sample and for generating a correction factor based on the value. The determining system also includes a calculator for calculating the final amount of pollutants based on the correction factor and the preliminary amount of pollutants.

Preferably, the control unit also generates a control signal based on: (1) the value for the amount of water vapor in the diluted sample; (2) the flow rate of the exhaust emissions; and (3) the type of fuel used in the combustion process.

The above objects and other objects, features, and advantages of the present invention are readily apparent from the following detailed description of the best mode for carrying out the invention when taken in connection with the accompanying drawings.

BEST MODE FOR CARRYING OUT THE INVENTION

Figure 4:
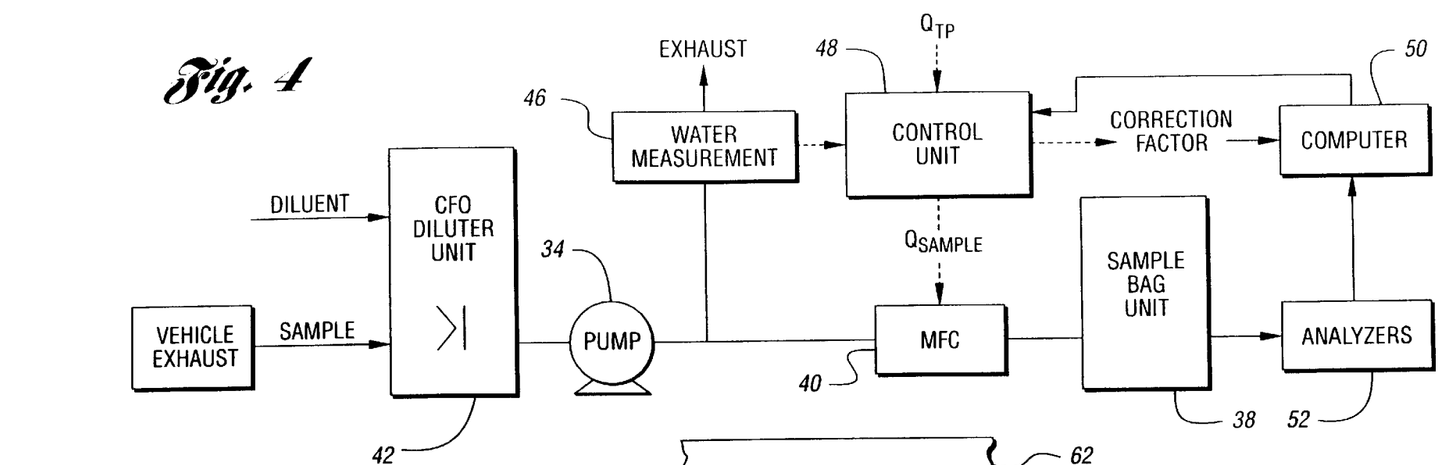
FIG. 4 is a schematic block diagram of an exhaust emission sampling system which utilizes the control method and system of the present invention.

Referring now to FIG. 4, there is illustrated with respect to the mini-diluter of FIG. 3, a control method and system of the present invention wherein the components of FIG. 4, which are the same as the components of FIG. 3, have the same reference numeral such as the pump 34, the mass flow controller 40, and sample bags or sample bag unit 38. A CFO diluter unit 42 of FIG. 4 includes the pressure regulator 30, the diluent and sample CFO's 38 and the oven 32 of FIG. 3.

The control method and system of the present invention provides a controlled portion of the flow of diluted sample to a water vapor measuring device such as a relative humidity sensor or transducer 46 which senses humidity and generates a corresponding water vapor signal based on the amount of water vapor in the diluted sample. Typically, humidity variations are converted to capacitance variations of the sensor 46 in a well known fashion.

The water vapor signal is then received by a controller or control unit 48 which is preferably a computer programmed to process the water vapor signal to determine the amount of water vapor in the diluted sample and to generate a control signal based on the amount. The control signal is used to control the mass flow controller 40 and, in particular, to control a control valve (not shown) within the controller 40 to vary the mass flow of the diluted sample therethrough.

The control signal (i.e. $Q_{sample}$ or $n_{bag}$) generated by the control unit 48 is also based on flow rate of the exhaust emissions from the vehicle (i.e. $Q_{Tp}$ or $n_{ex}$) and the type of fuel used in the combustion process. This latter information is provided by a computer 50 to the control unit 48.

The control unit 48 also calculates a correction factor (i.e. $F_{corr}$) based on the value for the amount of water vapor in the diluted sample. The correction factor is then supplied by the control unit 48 to the computer 50 which, in turn, calculates a final amount of pollutants in the exhaust emissions. This final amount is also based on a preliminary amount of pollutants provided by analyzers 52 after the analyzers 52 have analyzed the diluted sample for pollutants as is well known in the art.

Figure 5:
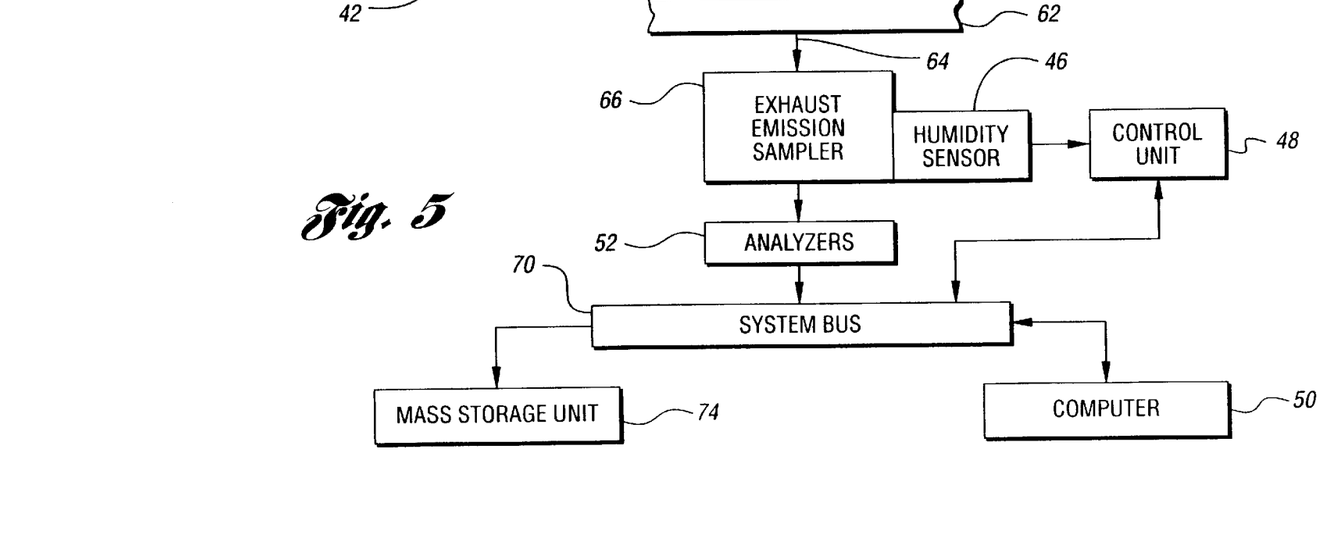
FIG. 5 is a schematic block diagram of an exhaust emission analyzing system which utilizes the determining method and system of the present invention.

Referring now to FIG. 5, there is illustrated a system for determining the final amount of pollutants in the exhaust emissions of an engine's combustion process. The components of the system of FIG. 5 which are the same as the components of FIG. 4 have the same reference numeral such as the sensor 46, the control unit 48, the analyzers 52, and the computer 50. Exhaust from an exhaust pipe 62 is fluidly coupled to an operating engine (not shown) and by a tailpipe adapter 64 to an exhaust emission sampler 66 such as the mini-diluter previously described. In general, the exhaust emission sampler 66 prepares a sample such as a diluted sample of exhaust gas for analysis by the exhaust emission analyzers 52 for analyzing the sample. The sampler 66 measures the concentration of exhaust substances (i.e. emissions of, for example, CO, $CO_2$, hydrocarbons (HC), $NO_x$, $SO_x$, and the like) contained in the exhaust gas of an engine such as the engine of an automotive vehicle.

The analyzers 52 typically measure concentration of the exhaust gases in the sample and provide corresponding exhaust gas concentration data to a system bus 70, which may be a standard bus, which allows intersystem communication such as to the computer 50, a mass storage unit 74, and a monitor (not shown).

The computer 50 may be a PC having a sufficient amount of RAM and hard disk space for performing the algorithms associated with the present invention.

The system of the present invention may be programmed at the mass storage unit 24 to include a predetermined set of calculations as described hereinbelow.

In general, and as described in mathematical terms hereinbelow, to correct for the effects of the changing water content in the diluted sample, the control method and system of the present invention preferably uses a humidity sensor that measures the actual humidity of the sampled, diluted gases. A correction value in the form of a control signal is fed back to the mass flow controller 40 to compensate for the effects of the changing water content on the dilution ratio that is established by the critical flow orifices.

Also, the determining method and system of the present invention also uses humidity readings to determine a correction factor which, in turn, is utilized by the computer 50 to obtain final amounts of pollutants compensated for changing water vapor.

Derivation of Mathematical Correction for Water Vapor

The object of a bag sampler and analytical system is to calculate the grams of a pollutant that are emitted over a test interval. The action of the diluting portion of the sampler is to dilute the sample by a known factor K, so that:

$$[P]_{sample} = \frac{n_P}{n_{ex} + n_{dil}} = \frac{n_P}{n_{ex} \cdot (1 + K)} = \frac{[P]_{raw}}{(1 + k)}$$

The action of the sampler that fills a sample bag at a flow rate proportional to the exhaust flow rate assures that:

$$n_{bag} \text{ (i.e. } Q_{sample}) = \alpha \cdot n_{ex} \text{ (i.e. } Q_{Tp})$$

The action of collecting the sample gases in a bag integrates these quantities. At the end of a test phase or bag filling interval, the concentration in the bag can be represented as:

$$[P]_{bag} = \frac{\int_0^{505} [P]_{sample} \cdot n_{bag} \cdot dt}{\int_0^{505} n_{bag} \cdot dt}$$

Substituting the above relationships, this can be written:

$$[P]_{bag} = \frac{\int_0^{505} \frac{[P]_{raw}}{(1+K)} \cdot \alpha \cdot n_{ex} \cdot dt}{\int_0^{505} \alpha \cdot n_{ex} \cdot dt}$$

Ideally, K and $\alpha$ are held constant, so they can be taken out from under the integral and we can write:

$$[P]_{bag} \cdot V_{tp} \cdot (1+k) = \int_0^\tau \frac{n_P}{n_{ex}} \cdot dt = \int_0^1 \cdot dt = \text{grams}_p$$

Which is the desired result: The grams from the test are obtained by multiplying the concentration in the bag by the total exhaust volume collected over the test phase, and applying a constant dilution factor.

A difficulty arises because the factor K is not constant because the composition of the sample gas is changing as the amount of water in its changes. A compensation can be made for this by adjusting the bag sample rate. If the dilution ratio increases, it can be compensated for by increasing the sample flow rate into the bags. In other words, one makes the proportionality constant $\alpha$ vary in time as K does. Specifically, one programs the control system so that:

$$\alpha(t) = \alpha_0 \cdot \frac{1 + k(t)}{1 + K_0}$$

Then the concentration in the bag becomes:

$$[P]_{bag} = \frac{\int_0^1 \frac{[P]_{raw}}{(1+K(t))} \cdot \alpha(t) \cdot n_{ex} \cdot dt}{\int_0^1 \alpha(t) \cdot n_{ex} \cdot dt} = \frac{\int_0^1 \frac{[P]_{raw}}{(1+K_0)} \cdot \alpha_0 \cdot n_{ex} \cdot dt}{\int \alpha(t) \cdot n_{ex} \cdot dt}$$

This concentration differs from the desired result because of the $\alpha(t)$ term in the denominator. However, the computer controller of the mini-diluter device can easily calculate this term and calculate a correction factor of the form:

$$F_{corr} = \frac{\int_0^1 \alpha(t) \cdot n_{ex} \cdot dt}{\int_0^1 n_{ex} \cdot dt}$$

The equation for the grams of pollutant becomes:

$$[P]_{bag} \cdot V_{tp} \cdot (1+K_0) \cdot F_{corr} = \text{grams}_p$$

This result provides a simple means to calculate the grams of pollutant from the concentration of a pollutant in a bag collected by the mini-diluter.

Dilution Constant, K

The flow of a gas through an orifice is given by:

$$Q = C_0 \cdot Y \cdot \pi \cdot \frac{d^2}{4} \cdot \sqrt{\frac{2\Delta P}{\rho \cdot (1 - \beta^4)}}$$

where Y is the expansion factor and $C_0$ is the coefficient of discharge. The expansion factor depends on the specific heat ratio, k, of the gas. The specific heat ratio depends on the composition of the gas.

$$Y := \left[\tau^{\frac{2}{k}} \cdot \left(\frac{k}{k-1}\right) \cdot \frac{1 - \tau^{\frac{k-1}{k}}}{1-\tau} \cdot \frac{1-\beta^4}{1 - \beta^4 \cdot \tau^{\frac{2}{k}}}\right]^{\frac{1}{2}}$$

When the pressure at the throat reaches a critical value, the speed of the flow in the throat reaches the speed of sound and the net flow cannot increase any further. The value for this critical pressure also depends on the specific heat ratio of the gas.

$$\Delta P = \left(1 - \left(\frac{2}{k+1}\right)^{\frac{k}{k-1}}\right) \cdot P_{inlet}$$

In the mini-diluter of FIG. 4, exhaust sample flows through one of the orifices 38 and diluent gas, for example $N_2$, flows through the other. The sample pump 34 upstream of the orifices 38 provides sufficient vacuum so that both are operating at critical flow. The specialized differential regulator 30 assures that the inlet pressure to both orifices 38 is the same, and the heated lines and cabinet insure that the temperatures at the orifices 38 are the same. Under these conditions, the amount of dilution is determined by the properties of these gases and the size of the orifices 38.

From the continuity of the flow:

$$Q_{md} = Q_{N_2} + Q_{samp}$$

It is convenient to introduce K, the ratio of the diluent gas (i.e. $N_2$ here) and sample flows, which is fixed by the orifice sizes and is a basic property of the mini-diluter.

$$K = \frac{Q_{N_2}}{Q_{samp}}$$

$$Q_{md} = (1+K) \cdot Q_{samp}$$

The value for K can be calculated from the orifice equation above. Using the ideal gas law and with appropriate cancellation of the common terms, this becomes:

$$K = \frac{C_{0_{N_2}} \cdot Y_{N_2} \cdot d_{N_2}^2 \cdot \sqrt{\frac{\Delta P_{N_2}}{M_{N_2} \cdot (1 - \beta_{N_2}^4)}}}{C_{0_{samp}} Y_{samp} \cdot d_{samp}^2 \cdot \sqrt{\frac{\Delta P_{samp}}{M_{samp} \cdot (1 - \beta_{samp}^4)}}}$$

The above equations describe the theoretically expected value for K. The mini-diluter of FIG. 4 also includes provisions for a calibration procedure that determines K with a direct measurement. This compensates for any uncertainties in the orifice dimensions or discharge coefficients. Plumbing is provided for calibration zero and span gases to be conducted through the orifices 38. The ratio of the concentration measured while calibration gas is conducted through both sample and diluent orifices 38 to the concentration measured while calibration gas is conducted through the sample orifice and diluent is conducted through the diluent orifice provides an empirical measure of K. An adjustment factor then accounts for differences between the composition of calibration and exhaust sample gases.

The Variation of K

As noted above, the dilution constant K varies with time because the amount of water vapor in the exhaust varies with time. In the above equation for K, it is $Y_{samp}$, $M_{samp}$ and $\Delta P_{samp}$ that vary as the water content of the sample changes. The changes in $Y_{samp}$ and $\Delta P_{samp}$ are due to small changes in the heat capacity ratio, k, and the change in $M_{samp}$ is due to the lighter density of water vapor. The appropriate values to use at any moment in time can be calculated from a knowledge of the water content of the sample, which is provided by the measurement device (i.e. sensor 46). The sensor 46, as previously mentioned, is a relative humidity sensor, a dewpoint sensor or a water concentration analyzer. Any of these provide a measurement of the water concentration that is used in the following way to compute the M and k values.

The molecular weight of the sample is given by:

$$M_{samp} = 18.0 \cdot [H_2O] + 44.0 \cdot [CO_2] + 28.0 \cdot [N_2]$$

And the heat capacity ratio of the sample is given by the following sequence of calculations:

$$k = \frac{C_p}{C_v} = \frac{C_p}{C_p - R}$$

$$C_p = 9.268 \cdot [CO_2] + 8.011 \cdot [H_2O] + 6.896 \cdot [N_2]$$

$$[H_2O] = \text{measured}$$

$$[CO_2] = \frac{x \cdot (1 - [H_2O])}{x + 3.774 \cdot \left(1 + \frac{y}{4} - \frac{z}{2}\right)}$$

$$[N_2] = \frac{3.774 \cdot \left(x + \frac{y}{4} - \frac{z}{2}\right) \cdot (1 - [H_2O])}{x + 3.774 \cdot \left(1 + \frac{y}{4} - \frac{z}{2}\right)}$$

where x, y and z are the atom counts in the molecular formula that represents the fuel. $C_p$ and $C_v$ are the heat capacities of the gases at constant pressure and volume, respectively, and R is the ideal gas constant. The values 9.268, 8.011 and 6.896 are the molar heat capacities of each species at the oven temperature.

The methods and systems of the present invention, as applied to the mini-diluter design of FIG. 4, offer a significant improvement over the CVS sampling techniques. The mini-diluter of FIG. 4 uses simpler and more reliable critical flow orifices 38 to fix the ratio of dilution of the sampled gases. The methods and systems of the present invention also apply to mass flow controllers, which are typically used where their weaknesses do not affect the measurement. The methods and systems of the present invention correct for the varying water content of sampled gases by measuring water content and feeding it back into the process.

While the best mode for carrying out the invention has been described in detail, those familiar with the art to which this invention relates will recognize various alternative designs and embodiments for practicing the invention as defined by the following claims.

What is claimed is:

1. In an exhaust emission analyzing system including an exhaust emission analyzer for analyzing a diluted sample to obtain a preliminary amount of pollutants, a determining system for determining a final amount of pollutants compensated for the effects of changing water vapor content in exhaust emissions from an engine's combustion process, the determining system comprising:

an exhaust emission sampler for preparing a diluted sample of exhaust emissions from an engine's combustion process;

a measuring device for generating a water vapor signal based on the amount of water vapor in the diluted sample;

a control unit for processing the water vapor signal to obtain a value for the amount of water vapor in the diluted sample and for generating a correction factor based on the value; and a calculator for calculating the final amount of pollutants based on the correction factor and the preliminary amount of pollutants wherein the final amount of pollutants is compensated for the effects of changing water vapor content in the exhaust emissions wherein the control unit also generates a control signal based on the value to control the flow of the diluted sample.

2. The determining system as claimed in claim 1 wherein the control unit generates the control signal also based on the flow rate of the exhaust emissions.

3. The determining system as claimed in claim 2 wherein the control unit also generates the control signal based on the type of fuel used in the combustion process.

* * * * *

UNITED STATES PATENT AND TRADEMARK OFFICE
CERTIFICATE OF CORRECTION

PATENT NO. : 5,968,452
DATED : October 19, 1999
INVENTOR(S) : William M. Silvis

It is certified that error appears in the above-identified patent and that said Letters Patent is hereby corrected as shown below:

On the title page, insert the following item:

-- [73] Assignee: Horiba Instruments, Inc., Ann Arbor, MI. --

Signed and Sealed this

Twenty-fifth Day of April, 2000

Attest:

Attesting Officer

Q. TODD DICKINSON
Director of Patents and Trademarks